United States Patent
Wissenwasser et al.

(10) Patent No.: US 9,300,161 B2
(45) Date of Patent: Mar. 29, 2016

(54) USE OF DEFINED FERROMAGNETIC MATERIALS FOR OPTIMIZED IMPLANT COIL COUPLING

(71) Applicant: MED-EL Elektromedizinische Geraete GmbH, Innsbruck (AT)

(72) Inventors: Jürgen Wissenwasser, Innsbruck (AT); Andreas Mitterer, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 517 days.

(21) Appl. No.: 13/871,081

(22) Filed: Apr. 26, 2013

(65) Prior Publication Data

US 2013/0285466 A1 Oct. 31, 2013

Related U.S. Application Data

(60) Provisional application No. 61/639,208, filed on Apr. 27, 2012.

(51) Int. Cl.
*H01F 27/42* (2006.01)
*H02J 7/02* (2006.01)
*H01F 38/14* (2006.01)
(Continued)

(52) U.S. Cl.
CPC .............. *H02J 7/025* (2013.01); *A61N 1/3787* (2013.01); *A61N 1/37229* (2013.01); *H01F 38/14* (2013.01)

(58) Field of Classification Search
CPC ........... H02J 17/00; H02J 5/005; H02J 7/025; H02J 3/01; H01F 38/14; B60L 11/182; B60L 11/1829; B60L 11/1831; Y02T 90/122; H04B 5/0037
See application file for complete search history.

(56) References Cited

U.S. PATENT DOCUMENTS 6,178,353 B1 1/2001 Griffith et al. .................. 607/61
6,327,504 B1 12/2001 Dolgin et al. .................. 607/61
(Continued)

OTHER PUBLICATIONS

International Searching Authority, Authorized Officer Blaine R. Copenheaver, International Search Report and Written Opinion—PCT/US2013/038325, date of mailing Sep. 24, 2013, 13 pages.

*Primary Examiner* — Jared Fureman
*Assistant Examiner* — Rafael Pacheco
(74) *Attorney, Agent, or Firm* — Sunstein Kann Murphy & Timbers LLP

(57) ABSTRACT

A coil arrangement is described for an implantable medical system. A coil winding has a planar ring shape winding that encloses a coil interior area. The coil winding is adapted for placement parallel to a corresponding partner coil for communication of an implant link signal having an associated magnetic field component characterized by a coupling factor k representing fractional amount of magnetic field coupling between the coils. A coil coupling lens of magnetic conductive material has multiple lens surfaces and is adapted to shape the magnetic field component to increase the coupling factor and minimize self-heating of adjacent tissues due to the magnetic field component. The lens surfaces include: i. an inner lens surface lying substantially parallel to the plane of the ring shape winding and having an inner lens surface perimeter enclosed within the coil interior area, ii. an outer lens surface lying substantially parallel to the inner lens surface and having an outer lens surface perimeter greater than the inner lens surface perimeter, and iii. at least one lens connecting surface connecting the inner lens surface perimeter and the outer lens surface perimeter.

11 Claims, 2 Drawing Sheets

(A)

(B)

(51) Int. Cl.
*A61N 1/378* (2006.01)
*A61N 1/372* (2006.01)

(56) References Cited

U.S. PATENT DOCUMENTS

| | | | |
|---|---|---|---|
| 6,478,820 B1 * | 11/2002 | Weiss | A61M 1/1086 607/61 |
| 6,617,853 B2 | 9/2003 | Bovier et al. | 324/320 |
| 2009/0261266 A1 * | 10/2009 | Lanio | B82Y 10/00 250/396 ML |
| 2010/0181843 A1 * | 7/2010 | Schatz | B60L 11/007 307/104 |
| 2011/0043047 A1 | 2/2011 | Karalis et al. | 307/104 |
| 2011/0087307 A1 | 4/2011 | Carbunaru et al. | 607/61 |
| 2011/0106210 A1 | 5/2011 | Meskens | 607/57 |

* cited by examiner (A)

(B)

USE OF DEFINED FERROMAGNETIC MATERIALS FOR OPTIMIZED IMPLANT COIL COUPLING

This application claims priority from U.S. Provisional Patent Application 61/639,208, filed Apr. 27, 2012, which is incorporated herein by reference.

FIELD OF THE INVENTION

The present invention relates to implantable medical devices, and specifically to energy transfer mechanisms in such devices.

BACKGROUND ART

Some active medical implants are powered by primary battery cells. Depending on their power consumption, they need to be replaced by new implants with new primary cells. The required surgery causes stress for the patients, various typical risks (e.g. infections, anaesthetic, etc.), and costs (new implant, operation costs, etc.).

Using rechargeable batteries in a medical implant can minimize the number of re-implantations and thereby reduce patient risk and cost. An implant with a rechargeable battery that provides tens of mAh of electric power (e.g., a rechargeable LiPo-battery) should have a recharge period that provides for patient comfort and acceptance. Typically that may be achieved by a charging power of 100 mW or higher.

Percutaneous implant connections can create surgical and medical risks such as risk of infections and biofilms by percutaneous connectors. Thus a wireless charging arrangement is usually preferable. This can be achieved using inductive links such as in the Precision Plus™ SCS System from Boston Scientific and the RestoreSensor/RestoreAdvanced/RestoreUltra SCS by Medtronic. Such inductive link arrangements generally use an external charger device on the patient's skin outside the body, which includes an external charging coil and necessary electronics. And there also is a corresponding internal coil being part of the implant. The coils are magnetically coupled by the inductive link with a power transfer an alternating magnetic field produced by the external coil, where some fraction k (coupling factor) of that field penetrates the skin to the implant coil which induces a voltage that drives current for the implant electronics.

For a given distance between transcutaneous induction coils, the magnetic coupling is primarily a function of the coil shapes, which typically are circular or spiral. Ideally the best coupling factor can be achieved if both coils have the same diameter, which should be at least √2 times the distance between the coils. See e.g., K. Finkenzeller, *RFID Handbook Fundamentals and Applications in Contactless Smart Cards and Identification*, (3rd ed.), Wiley, Hoboken, N.J. (2010), incorporated herein by reference. For example, given a coil distance 20 mm, optimal coupling requires a coil radius of 28 mm, which is too large for most implants.

For the patient's convenience, the external charging device should be compact and portable with its own integrated battery. To keep such an external device small and to minimize self-heating of adjacent tissues from eddy currents, the energy transfer needs to be efficient. Eddy current induced self-heating is not just uncomfortable, but temperature upper limits are also set by laws and regulations.

The Medtronic charging device is a quite bulky system running at a frequency of 175 kHz that reportedly suffers from significant self-heating issues. A similar problem is reported by St. Jude Medical. U.S. Pat. No. 7,599,744 (incorporated herein by reference) describes a transcutaneous coil arrangement that uses a rod made of soft iron which redirects the magnetic field lines in a defined way.

SUMMARY OF THE INVENTION

Embodiments of the present invention are directed to a coil arrangement for an implantable medical system. A coil winding has a planar ring shape winding that encloses a coil interior area. The coil winding is adapted for placement parallel to a corresponding partner coil for communication of an implant link signal having an associated magnetic field component characterized by a coupling factor k representing fractional amount of magnetic field coupling between the coils. A coil coupling lens of magnetic conductive material (e.g., ferromagnetic material such as soft iron) has multiple lens surfaces and is adapted to shape the magnetic field component to increase the coupling factor and minimize self-heating of adjacent tissues due to the magnetic field component. The lens surfaces include: i. an inner lens surface lying substantially parallel to the plane of the ring shape coil winding and having an inner lens surface perimeter enclosed within the coil interior area, ii. an outer lens surface lying substantially parallel to the inner lens surface and having an outer lens surface perimeter greater than the inner lens surface perimeter, and iii. at least one lens connecting surface connecting the inner lens surface perimeter and the outer lens surface perimeter.

In specific embodiments, the inner lens surface may lie substantially in the plane of the ring shape winding, or above or below the plane of the ring shape winding. The coil winding may be an implantable receiver coil and the partner coil would be an external transmitter coil, or vice versa. There also may be an electronics module enclosed within the coil coupling lens. Either or both of the inner and outer lens surfaces may have a planar ring shape enclosing a lens interior area, or a planar disk shape.

DETAILED DESCRIPTION OF SPECIFIC EMBODIMENTS

Various embodiments of the present invention are directed to an inductive coil arrangement for medical implants that optimizes the coupling factor of the inductive link using a specially formed coil coupling lens of ferromagnetic material having a magnetic permeability significantly larger than the surrounding tissue and air. Those materials in such a coil coupling lens modify the shape of the magnetic field component of the inductive link signal and thereby maximize the fraction of the magnetic flux (coupling factor) between the two coils. As used herein, the term "link signal" refers to an inductive transcutaneous electromagnetic signal which may contain just an energy component, or one which includes both an energy component and a data communications component.

An alternating magnetic field generally leads to eddy currents in the adjacent human tissue. This loss needs to be compensated for by a sufficiently strong charging field.
}

Depending on the effective charging power received by the implant, the external charging device and the tissue penetrated by the magnetic field, the surrounding tissue may become warm and even uncomfortably hot. In that case, the charging process needs to be interrupted or the charging power needs to be reduced, leading to undesirable increased charging time. Thus fast charging at elevated temperature is replaced by slower charging with reduced heating. An increased coupling factor k optimizes the power transfer efficiency, less current for the charger coil is needed, and the necessary magnetic field is reduced. Hence self-heating of external charging device is reduced and thus a short charging period at minimal heat dissipation is maintained. Furthermore, the reduced power loss allows the use of smaller batteries within the external charging device and temperature-related aging of electronics and mechanical components is reduced.

Figure 1:
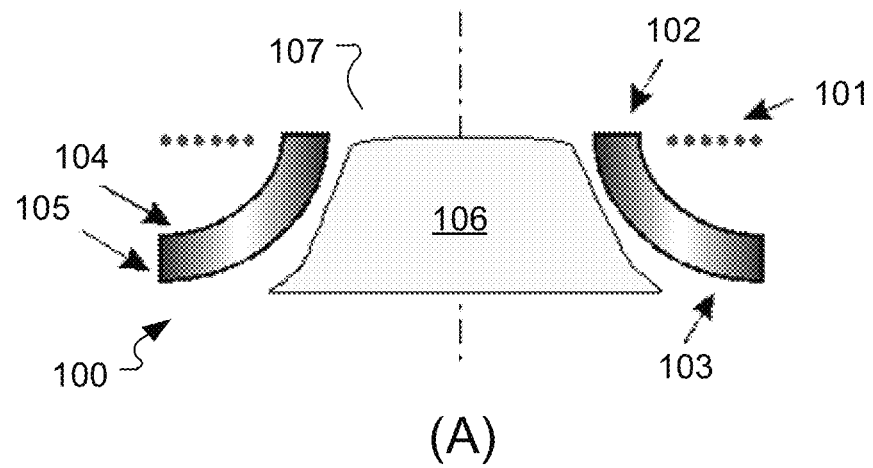
FIG. 1A-B shows a side cross-section and top plan view of a coil arrangement according to one embodiment of the present invention.
Figure 1:
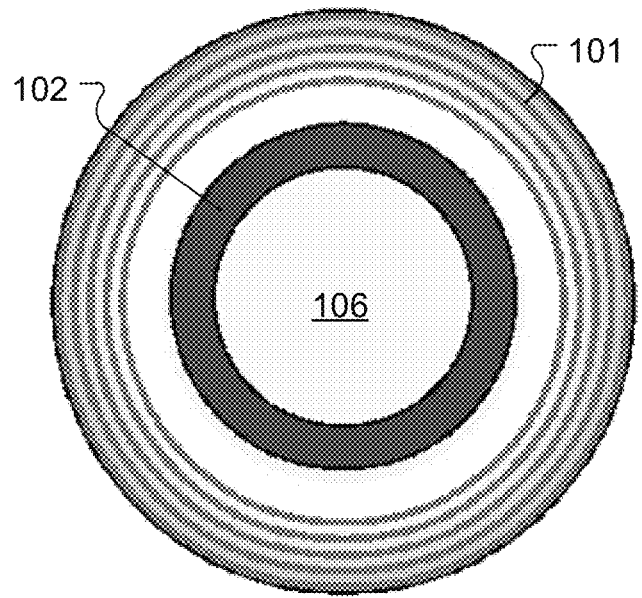

FIG. 1 A-B shows a side cross-section and top plan view respectively of a compact and efficient coil arrangement according to one embodiment of the present invention. A planar coil winding 101 has a ring shape that encloses a coil interior area 107. The coil winding 101 is adapted for placement parallel to a corresponding partner coil (not shown) for communication of an implant link signal having an associated magnetic field component that is characterized by a coupling factor k which represents the fractional amount of magnetic field coupling between the two coils.

The top plan view of the coil winding 101 shown in FIG. 1B is a circular ring, but the planar coil winding may have some other specific shape such as elliptical, oval, or polygonal with some number of sides. Depending on the implant's position inside the patient's body, the distance between the two coils may vary from a few millimeters to several centimeters.

Cooperating with the coil winding 101 is a coil coupling lens 100 of magnetic conductive material (e.g., ferromagnetic material such as soft iron) that has multiple lens surfaces and which is adapted to shape the magnetic field component of the link signal so as to increase the coupling factor and minimize self-heating of adjacent tissues. The surfaces of the coil coupling lens 100 include an inner lens surface 102 that lies substantially parallel to the plane of the coil winding 101 and has an inner lens surface perimeter enclosed within the coil interior area 107. In specific embodiments, the inner lens surface 102 may lie in the same plane as the coil winding 101, or above or below the plane of the coil winding 101. An outer lens surface 103 lies substantially parallel to the inner lens surface 102 and has an outer lens surface perimeter which is greater than the inner lens surface perimeter. At least one lens connecting surface connects the inner lens surface perimeter and the outer lens surface perimeter. In the embodiment shown in FIG. 1A, there is an inner lens connecting surface 104 and an outer lens connecting surface 105. As shown in FIG. 1A, the outer lens connecting surface 105 is substantially perpendicular to the inner lens surface 102 and the outer lens surface 103.

In specific embodiments, coil arrangements using a coil coupling lens 100 may be used in either or both of the external transmitter device and/or in the implant device. The ferromagnetic material of the coil coupling lens 100 possesses a high magnetic permeability which leaves the coil interior area 107 with just a low magnetic field component which is suitable for magnetically sensitive electronic circuitry such as the signal processing circuits of the implant. Such an open form coil coupling lens 100 may be especially useful in the implanted portion of the system—the implant electronics are often enclosed within a titanium housing which can be placed within the hollow interior volume of the coil coupling lens 100 which may reduce power losses due to eddy currents and self-heating of adjacent tissues.

The coil coupling lens 100 also may contain one or more through bores which may be threaded for fastening the device to underling bone, or unthreaded (e.g., for ventilation purposes). In addition or alternatively, the coil coupling lens 100 may further include one or more fastener protrusions so as to allow a secure placement of circuit boards within the device and/or of the device to underlying bone.

Figure 2:
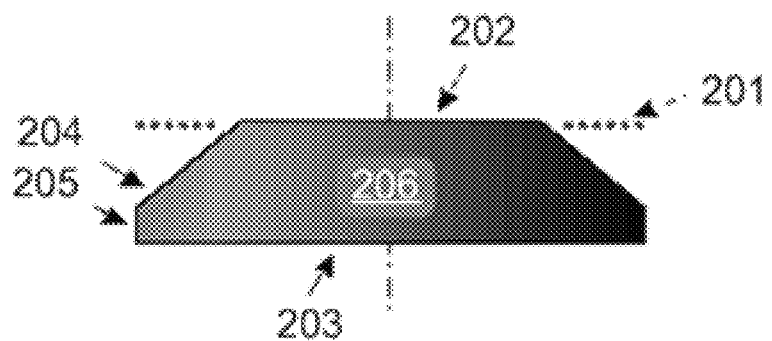
FIG. 2 shows a side view of another embodiment of the present invention.

The coil interior area 107 of the coil winding 101 may be circular, elliptical, oval, polygonal, etc. and may or may not be entirely or partially filled by a ferromagnetic material having a magnetic permeability larger than one, e.g. as shown in FIG. 2. In such an embodiment the entire area within the ring shaped coil winding 202 is filled by the inner lens surface 202, and the coupling lens device entirely fills the volume defined by the inner lens surface 202, the outer lens surface 203, and the lens connecting surfaces 204 and 205.

Figure 3:
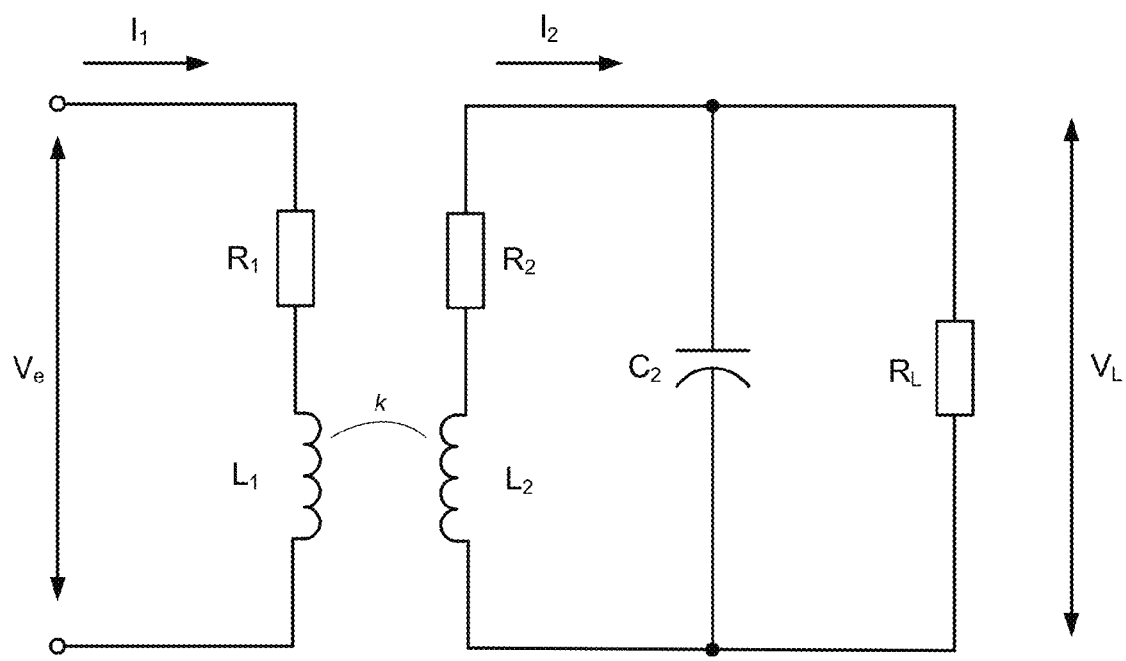
FIG. 3 shows a simplified equivalent circuit of an inductive link as in embodiments of the present invention.

FIG. 3 shows a simplified equivalent circuit of an inductive link for an implant system using a coupling lens according to embodiments of the present invention. An external charger transmitter coil has an inductance $L_1$ and ohmic resistance $R_1$. An implant device has a receiver coil with an inductance $L_2$, ohmic resistance $R_2$, internal capacitance $C_2$, and load resistance $R_L$. An alternating voltage is applied to the external charger circuit with an RMS value of $V_e$ and frequency f, to produce an external circuit current $I_1$. This induces a voltage in inductance $L_2$ leading to a load voltage $V_L$ across the load resistance $R_L$ producing load current $I_2$.

A mathematical transformation is conducted which makes the characteristic impedance $Z_I$ of the implant circuit act as a series impedance $Z_I'$ in the external charger coil circuit:

$$Z_I' = k^2 \omega^2 L_1 L_2 \cdot [R_2 + j\omega L_2 + R_L/(1+j\cdot \omega R_L C_2)]^{-1}$$

where $\omega = 2*\pi*f$ is the circular frequency. With a resonant implant circuitry, i.e. $\omega^2 \cdot L_2 \cdot C_2 = 1$, that impedance is:

$$Z_{I,res}' = k^2 \omega^2 L_1 L_2 \cdot [R_2 + j\omega L_2 + R_L/(1+j\cdot R_L/\omega/L_2)]^{-1}$$

First the transmission efficiency $\eta_1$ is defined as the transmitted power in relation to the overall power:

$$\eta_1 = I_1^2 * \Re\{Z_I'\}/[I_1^2 * \Re\{Z_I'\} + I_1^2 * R_1] = \Re\{Z_I'\}/[\Re\{Z_I'\} + R_1]$$

Second, the implant efficiency $\eta_2$ (with $\omega^2 \cdot L_2 \cdot C_2 = 1$ for resonance):

$$\eta_2 = [1 + R_2 R_L \cdot (R_L^{-2} + \omega^{-2} L_2^{-2})]^{-1}$$

That value is important with respect to the implant self-heating. If a given implant embodiment has a certain maximum power loss with respect to the surrounding tissue, that efficiency must have a minimum value for a given load or else the load needs to be reduced.

The overall system efficiency $\eta_{oa}$ can be defined as the scalar product of those external and implant efficiencies, i.e. $\eta_{oa} = \eta_1 * \eta_2$. This overall efficiency should be as large as possible. For a given frequency f, the inductive parameters $L_1$ and $L_2$ can be modified, and $R_1$ and $R_2$ are given by the conductor materials of the coil loops. The coupling factor k is defined by the coil shapes and their relative geometrical position and angle.

An external charging current $I_1$ flowing through $R_1$, $L_1$ and the impedance $Z_I'$ leads to a transmitted power to the implant which equals $I_1^2 \cdot \Re\{Z_I'\}$. In the implant, this power is divided into a power loss on $R_2$ and a useable load power on $R_L$. The $R_1$ power is lost equal to $I_1^2 \cdot R_1$.

For example, if the external charger transmitting coil has a diameter of 60 mm, and the diameter of the implant receiver coil is 30 mm, then the coupling factor at a distance of 40 mm (with coaxial coils) is less than 4%. The external transmitter coil may have a resistance $R_1=700$ m$\Omega$ while $\Re\{Z_I'\}=400$ m$\Omega$. To transfer 200 mW of power, the necessary external charger coil current is $I_1=(200\text{ mW}/400\text{ m}\Omega)^{1/2}=707$ mA. The power loss on $R_1$ is $(0.707\text{ A})^2*700$ m$\Omega=350$ mW. While that loss on the external charger transmitter coil might not necessarily cause a harmful temperature increase, it may be of importance where the external device is powered by a battery. The relatively high current flowing through the transmitter coil can have two severe effects:

- For active components such as RF-generator components for voltage $V_E$, the power losses significantly decrease overall performance, and
- In many cases external capacitors will be placed in series with the transmitter coil in order to reduce the imaginary impedance. Voltages of more than 100 V may be found at those capacitors which in turn require a higher voltage rating of those devices and an additional isolation may be required.

If the coupling factor k could be increased by just 20%, then the quadratic influence of that value on $\Re\{Z_I'\}$ would lead to a new $Z_{I,mod}'$ with $\Re\{Z_{I,mod}'\}=(1+20\%)^2*\Re\{Z_I'\}=1.44*400$ m$\Omega=1008$ m$\Omega$. A recalculation will then lead to a current $I_{I,mod}=(200\text{ mW}/1008\text{ m}\Omega)^{1/2}=445$ mA with a power loss on $R_1$ of $(0.445\text{ A})^2*700$ m$\Omega=139$ mW. Thus a coupling increase of 20%:

- decreases the coil current by 37%,
- and in turn decreases power loss on $R_1$ by 40%.
- Furthermore, the previously mentioned capacitors may also have a voltage rating which is 37% lower, and the current rating for additional active components, such as the RF-generator for the applied voltage $V_E$, is also significantly reduced.

Similar optimized shaping of the magnetic field can be applied on the implanted receiver coil, resulting in additional increase of coupling by 20%, further decrease of coil current, decrease in power loss in $R_1$, further reduced voltage rating of the capacitors, and further reduced current rating of active components.

The ferromagnetic material of the coil coupling lens also may act as a magnetic shielding to minimize parasitic voltages induced in the electronics of the charger device. Therefore, electronic parts can be implemented in the housing of the charging coil which otherwise might not be possible. Reduced radiation improves electromagnetic compatibility and so the magnetic material may also be used for that purpose to shape the magnetic field component of the link signal.

Although various exemplary embodiments of the invention have been disclosed, it should be apparent to those skilled in the art that various changes and modifications can be made which will achieve some of the advantages of the invention without departing from the true scope of the invention.

What is claimed is:

1. A coil arrangement for an implantable medical system, the arrangement comprising:

a coil winding having a planar ring shape winding enclosing a coil interior area and adapted for placement parallel to a corresponding partner coil for communication of an implant link signal having an associated magnetic field component characterized by a coupling factor k representing fractional amount of magnetic field coupling between the coils; and a coil coupling lens of magnetic conductive material with a plurality of lens surfaces adapted to shape the magnetic field component to increase the coupling factor and minimize self-heating of adjacent tissues due to the magnetic field component;

wherein the lens surfaces include:
   i. an inner lens surface lying substantially parallel to the plane of the ring shape winding and having an inner lens surface perimeter enclosed within the coil interior area,
   ii. an outer lens surface lying substantially parallel to the inner lens surface and having an outer lens surface perimeter greater than the inner lens surface perimeter, and
   iii. at least one lens connecting surface connecting the inner lens surface perimeter and the outer lens surface perimeter.

2. An arrangement according to claim 1, wherein the inner lens surface lies substantially in the plane of the ring shape winding.

3. An arrangement according to claim 1, wherein the inner lens surface lies above or below the plane of the ring shape winding.

4. An arrangement according to claim 1, wherein the coil winding is an implantable receiver coil and the partner coil is an external transmitter coil.

5. An arrangement according to claim 1, wherein the coil winding is an external transmitter coil and the partner coil is an implantable receiver coil.

6. An arrangement according to claim 1, further comprising:

an electronics module enclosed within the coil coupling lens.

7. An arrangement according to claim 1, wherein the inner lens surface has a planar ring shape enclosing an inner lens interior area.

8. An arrangement according to claim 1, wherein the inner lens surface has a planar disk shape.

9. An arrangement according to claim 1, wherein the outer lens surface has a planar ring shape enclosing an outer lens interior area.

10. An arrangement according to claim 1, wherein the outer lens surface has a planar disk shape.

11. An arrangement according to claim 1, wherein the coil coupling lens includes ferromagnetic material.

* * * * *